United States Patent [19]

Levenbook et al.

[11] Patent Number: 5,550,018
[45] Date of Patent: Aug. 27, 1996

[54] TEST FOR VIRULENT GENOMIC NUCLEOTIDE 472 REVERTANTS IN ATTENUATED LIVE POLIOVIRUS TYPE 3 VACCINES

[75] Inventors: Inessa Levenbook; Konstantin Chumakov, both of Bethesda; Laurie Powers, Silver Spring, all of Md.; Igor Roninson, Chicago, Ill.

[73] Assignee: The United States of America as represented by the Department of Health and Human Services, Washington, D.C.

[21] Appl. No.: 246,373

[22] Filed: May 18, 1994

Related U.S. Application Data

[63] Continuation of Ser. No. 607,742, Nov. 6, 1990, abandoned.
[51] Int. Cl.$^6$ ............... C12Q 1/70; C12Q 1/68
[52] U.S. Cl. ............... 435/5; 424/184.1; 424/204.1; 424/217.1; 424/93.1; 424/93.6; 435/6; 435/91.2; 435/91.32; 435/91.33; 435/91.5; 435/172.1; 435/173.3; 435/236; 435/237; 536/24.1; 536/24.31; 536/24.33; 935/77; 935/78
[58] Field of Search ............... 424/184.1, 185.1, 424/199.1, 204.1, 217.1, 93.2, 93.6; 435/5, 6, 91.2, 91.32, 91.33, 91.5, 91.51, 172.1, 173.3, 235.1, 236, 237, 948; 436/501, 63; 536/23.1, 24.1, 24.3–.33; 935/77, 78

[56] References Cited

U.S. PATENT DOCUMENTS

| | | | |
|---|---|---|---|
| 4,683,195 | 7/1987 | Mullis et al. | 435/6 |
| 5,286,640 | 2/1994 | Almond et al. | 435/236 |
| 5,298,413 | 3/1994 | Almond et al. | 435/236 |
| 5,298,416 | 3/1994 | Almond et al. | 435/236 |

OTHER PUBLICATIONS

Almond, Ann. Rev. Microbiol., 41:153–80 (1987).
Weeks–Levy et al, Vaccines, 88:223–227 (1988).
Mento et al., Abstract in: Proceedings of the 5th Meeting of the European Group on Pronnaviruses, Mallorea, Spain (1987).
Nature, vol. 314, issued 11 Apr. 1985, Evans et al, "Increased neurovirulence associated with a single nucleotide change in noncoding region of Sabin type 3 polivaccine genome", pp. 548–550.
Proceedings of the National Academy of Science USA, vol. 81, issued Mar., 1984, Stanway et al, "Comparison of the complete nucleotide sequence of the genomes of the neurovirulent poliovirus P3/Leon/37 and its attenuated Sabin vaccine derivates P3/Leon 12a1b", pp. 1539–1543.

(List continued on next page.)

*Primary Examiner*—Margaret Parr
*Assistant Examiner*—Ardin H. Marschel
*Attorney, Agent, or Firm*—Needle & Rosenberg, P.C.

[57] ABSTRACT

The present invention comprises the method of evaluation of the safety of live attenuated vaccines based on detection and measurement of the incidence of genetic changes associated with reversion to virulence in vaccine microorganisms. The method based on PCR and restriction enzyme analysis was developed and used for determination of the proportion of mutants contributing to neurovirulence of type 3 live oral poliovirus vaccine. The correlation between the neurovirulence of OPV lots revealed by the monkey test and the abundance of mutant virus containing cytidine in the position 472 was discovered. The amount of these mutants increases upon passages of the virus in cell cultures at a rate dependent on the cell type, cultivation conditions and the seed virus stock. The present invention can be applied for the safety test of lots of live vaccines and in-process control of vaccine manufacturing as well as the approach for optimization of conditions for manufacturing of safe vaccine and selection of the seed virus and cell substrate.

5 Claims, 6 Drawing Sheets

OTHER PUBLICATIONS

The Journal of General Virology, vol. 67, issued 1986, Hughes et al., "The nucleotide sequence of a type 3 poliovirus isolated during a recent outbreak of Poliomyelitis in Finland", pp. 2093–2102.

The Journal of Virology, vol. 170, issued 1989, Kinnunen et al, "Partial RNA sequencing of eight supposed derivatives of type 3 poliovirus/USA/Saukett/50 reveals remarkable differences between three apparent substrains", pp. 316–320.

The Journal of Molecular Biology, vol. 174, issued 1984, Toyoda et al, "Complete nucleotide sequences of all three poliovirus serotype genomes", pp. 561–585.

The Journal of Virology, vol. 63, No. 3, issued Mar., 1989, Westrop et al, "Genetic basis of attenuation of the Sabin type 3 oral poliovirus Vaccine", pp. 1338–1344.

The Journal of Virology, vol. 175, issued 1990, Svitkin et al, "Translation Deficiency of the Sabin Type 3 Poliovirus Genome: Association with an Attenuating Mutation $C_{472}$ U", pp. 103–108.

Stenway et al. Nu. Acids Res. 11(16):5629 (1983).

FIG. 6 ns the 5' side of the marker. More specifically two oligonucleotides flank the marker sequence, bind to the opposite strands of DNA and serve as primers for PCR leading to amplification of marker-containing DNA sequence. The tested genetic changes would be detected by the appearance or disappearance of a characteristic restriction site, which may be present in the vaccine or revertant specific nucleotide sequence or artificially created by modifying the sequence of at least one of the oligonucleotides.

TEST FOR VIRULENT GENOMIC NUCLEOTIDE 472 REVERTANTS IN ATTENUATED LIVE POLIOVIRUS TYPE 3 VACCINES

This application is a continuation of application Ser. No. 07/607,742, filed Nov. 6, 1990 now abandoned.

BACKGROUND OF THE INVENTION

The currently used live poliomyelitis vaccine developed by Sabin (Sabin, A. B. Ann N.Y. Acad. Sci. 61 :924–938 (1955); Sabin, A. B., PASB Sc. Pub. 44: 14–33 (1959); Sabin, A. B., J. Am. Med. Assoc. 194:130–134 (1965)) comprises three attenuated viral strains, corresponding to poliovirus type 1, type 2 and type 3. These vaccines, although very safe and effective, are nevertheless genetically unstable and prone to reversion to neurovirulence. Therefore, each new batch of vaccine requires vigorous safety testing. The only test which has been used for neurovirulence testing of vaccine lots is performed by intrathalamic and/or intraspinal inoculation of monkeys with subsequent pathological evaluation of developing lesions. This test is very expensive, slow and its results may vary since individual responses of monkeys to the inoculum may differ significantly. The same problems are shared by animal safety tests used for other live attenuated vaccines.

Type 3 poliovirus vaccines have been most frequently associated with vaccine-associated cases of polyomyelitis and require the most rigorous animal testing. Studies on type 3 viruses excreted by healthy children after ingestion of the trivalent oral polio vaccine (OPV) regularly showed a change in the nucleotide at position 472 from uridine (U), found in the genome of the type 3 vaccine strain, to cytosine (C), found in wild type strains (Stanway et al, Proc. Natl. Acad. Sci. USA, 81:1539–1543 (1984); Evans et al, Nature, 314:548–550 (1985) and Westrop et al, J. Virol., 63:1338–1344 (1989)). The same mutation was shown to be present in isolates from cases of vaccine-associated disease (Almond, Ann. Rev. Microbiol., 41:153–180 (1987)). This mutation was shown to result in a quantitative increase in histologic lesions scores produced in monkeys after intraspinal inoculation of the virus (Evans et al, Nature, 314:548–550 (1985) and Westrop et al, J. Virol., 63:1338–1344 (1989)).

Sequence changes in poliovirus RNA have been previously analyzed by direct sequencing of viral RNA (Evans et al, Nature, 314:548–550 (1985) and Weeks-Levy et al, Vaccines, 88:223–227, Cold Spring Harbor Laboratory Press, Cold Spring Harbor, N.Y. (1988)), a method which is not particularly sensitive for detection of sequence variants present at low abundance. This approach failed to reveal mutants at position 472 in type 3 poliovirus vaccine lots (Weeks-Levy et al, Vaccines, 88:223–227, Cold Spring Harbor Laboratory Press, Cold Spring Harbor, N.Y. (1988)).

SUMMARY OF THE INVENTION

There is a need to develop alternative tests for the stability of attenuated vaccine microorganisms. The best conceivable test would address the issue of stability directly, by analyzing specific genetic changes in the microorganisms, associated with reversion to pathogenicity, rather than indirectly by animal safety tests.

The essence of the present invention is the method of evaluation of live attenuated vaccines based on detection and measurement of the incidence of genetic changes associated with reversion to virulence in the vaccine microorganisms. The diagnostic test determines the presence and measures the incidence of DNA or RNA sequences associated with the reversion (marker). The present invention demonstrates that the frequency of such genetic changes correlates with the vaccine safety as determined by the monkey test. Vaccines which pass the test can be administered to patients.

The present invention is also directed to a kit for determining and measuring revertant microorganisms in a vaccine which contains the essential materials for conducting the diagnostic test. When the diagnostic test is based on polymerase chain reaction (PCR) technology, the kit will contain at least a first oligonucleotide which selectively binds to RNA or DNA on the 3' side of the marker and a second oligonucleotide which selectively bi The present invention can also be used to test for changes in the incidence of revertant microorganisms grown in a cell culture which is used, or which may be used, in vaccine production to determine the rate of reversion of microorganism in the cell culture. In accordance with this aspect of the invention, an attenuated live vaccine is cultured in a cell culture for a predetermined period of time and then a test is conducted to determine the incidence of revertants in the microorganism. Cell cultures or microorganism strains that exhibit the lowest incidence of revertants would therefore be optimal for the vaccine production. Such cultures or strains also constitute the subject of the present invention.

BRIEF DESCRIPTION OF THE DRAWINGS

FIG. 2 is an autoradiogram of a polyacrylamide gel containing MboI-digested PCR products. Lanes 1–9 represent the analysis of mixtures of standard 472-T and 472-C DNAs containing 100, 5, 2.5, 2, 1.5, 1, 0.5, 0.2 and 0% of 472-C, respectively. Lanes 10–15 represent the analysis of RNA from different batches of polio vaccine type 3, including three batches that failed monkey neurovirulence tests (lanes 10–12) and three batches that passed these tests (lanes 13–15). Bands corresponding to the undigested 93-bp (A) and MboI-digested 61-bp (B) PCR products are indicated with arrows. The presence of a small amount of the 61-bp fragment in lane 9, containing 100% 472-T, visible in the original autoradiogram but poorly reproduced in the photograph, apparently indicates low-level misincorporation of a C residue at position 472 during PCR.

DETAILED DESCRIPTION OF THE INVENTION

As used in the present application, the term "marker" refers to a difference or differences between the nucleotide sequence of a virulent form of a microorganism, particularly a virus, and the nucleotide sequence of a corresponding attenuated microorganism used in the vaccine. The marker can be a single difference (one point difference) in a nucleotide sequence or differences in more than one nucleotide, wherein the different nucleotides are located in close proximity to each other.

The term "revertant" refers to a microorganism with increased virulence regardless of whether the reversion is caused by the restoration of the original nucleotide sequence present in the original pathogenic strain or by the novel mutation in the genome of a vaccine microorganism leading to increased virulence.

The term "vaccine" refers to a pharmaceutical preparation containing an attenuated live microorganism and usually also a pharmaceutically acceptable sterile carrier.

The present invention has potential use in the detection of revertants of various types of microorganisms. Initial work has been performed on the poliovirus. However, the present invention has possible use with other types of viruses which are used to make vaccines, particularly those viruses which are prone to reversion. Other possible types of vaccine viruses are attenuated strains of mumps, measles, rubella, varicella, Dengue, Venezuelan equine encephalitis, Eastern equine encephalitis, vaccinia, rotaviruses, influenza etc. It is also possible that the present invention can be used to detect revertants or mutants in rickettsial (Strain E) and bacterial vaccines such as BCG, live vaccine against plague, tularemia, brucellosis, anthrax, typhoid fever and shigellosis.

Various types of tests can be used to test for the presence of revertant microorganisms. At the present time, PCR amplification and restriction enzyme digestion are preferably used to test for the presence of revertants. However, it is possible that other tests such as hybridization with specific oligonucleotides, RNAse protection, chemical cleavage assays or assays based on ligation of specific oligonucleotides could also be used to test for revertants.

When PCR technology is used to test for the revertants, different procedures can be used to label the amplified sequence. For example, the anti-sense primer can be labeled with $P^{32}$, the sense primer can be labelled with $P^{32}$ or one of the nucleotides in the nucleotide mix which is used to create the amplified sequences can be labeled. Non-radioactive labelling such as enzyme-based assays, chemiluminescence, and fluorescence energy transfer can also be used, as well as sensitive methods for detection of unlabelled DNA. Separation of DNA fragments can be achieved by methods other than gel electrophoresis. For example, DNA fragments produced by restriction enzyme cleavage can be separated and quantitated by high performance liquid chromatography (HPLC).

The oligonucleotides used as primers should contain enough nucleotides so that they specifically bind only to the desired nucleotides, sequence usually at least about 8 nucleotides, preferably 10 to 50 nucleotides, more preferably 15 to 40 nucleotides. The oligonucleotides should bind to regions in close proximity to the marker under investigation. The region amplified by PCR technology will usually have a length of about 60 to 600 nucleotides.

Amplification of the marker-containing region by PCR is convenient since it allows one to use very small amounts of RNA or DNA from the vaccine microorganism for the test. It is possible, however, to detect and measure the marker directly using the genomic DNA, RNA or cCDNA synthesized from genomic RNA of the vaccine microorganism, without amplifying the marker-containing region by PCR or any other technique.

The preferred procedure for detection of the marker associated with reversion to virulence consists of digestion of the marker-containing DNA segment with a restriction enzyme which cuts the DNA only if the marker sequence is present, followed by measuring the proportion of DNA digested with the above restriction enzyme. The marker-specific restrictions site may pre-exist in the DNA sequence of the revertant, or it may be created by modifying the sequence of cDNA or of the PCR-amplified segment by making appropriate changes in at least one oligonucleotide used for cDNA synthesis or for PCR. Alternatively, the reversion marker may be detected by the absence rather than by the presence of a restriction site. The marker can also be detected and measured by hybridization with marker-containing oligonucleotide probes corresponding either to the vaccine-specific or to the revertant-specific sequences, followed by comparison of the hybridization signal obtained with each of the probes. It is also possible to carry out PCR amplification using two pairs of oligonucleotides, one selected so as to selectively amplify the revertant sequence; the yields of the two PCR reactions can then be compared to each other to determine the incidence of the revertant. Furthermore, the same markers can also be detected and measured by denaturation of double-stranded DNA, RNA or cDNA or the vaccine microorganism, followed by reassociation and detection of mismatched duplexes by cleavage with enzymes or chemical reagents that specifically recognize mismatched DNA or RNA duplexes, with subsequent measurement of the cleavage products.

MATERIALS AND METHODS

Virus growth, RNA isolation and cDNA preparation.

Viral RNA was isolated directly from 0.4 ml of vaccine stocks or cell culture fluid by phenol extraction with 1% SDS. African green monkey kidney (AGMK) cells were obtained from Quality Biologics Inc. (Gaithersburg, Md.) and infected either with 0.1 tissue culture doses ($TCD_{50}$) per cell ("low multiplicity") or 10 $TCD_{50}$/cell ("high multiplicity") or the appropriate virus stock. cDNA was synthesized with Mo-MuLV reverse transcriptase (SuperScript™, Bethesda Research Laboratories) and random hexadeoxynucleotide primers (Noonan et al, Nucleic Acids Res., 16:10366 (1988)).

Analysis of 472-T to 472-C mutants.

PCR amplification of a cDNA segment between positions 440–532 in poliovirus type 3 RNA (Toyoda et al, J. Mol. Biol., 174:561–585 (1984)) was carried out using Taq DNA polymerase (AmpliTaq™, Perkin-Elmer/Cetus) for 30 cycles (each cycle included 1 min at 94° C. and 5 min at 65° C.) The sense strand PCR primer (pS) was (SEQ ID No:1), corresponding to positions 440–471 of poliovirus type 3 RNA except for an A to G change at position 469. This change creates a HinfI restriction site in PCR products amplified from vaccine-specific sequences and an MboI restriction site in PCR products amplified from revertant-specific sequences. The antisense strand PCR primer (pA) was (SEQ ID NO:2), complementary to positions 502–532 of poliovirus type 3 RNA. The pA primer was 5'-end labeled with gamma-[$^{32}$P]-ATP (Amersham) prior to PCR. Each reaction contained 0.5 μg of the pS primer and 0.05 μg of the [$^{32}$P]-labeled pA primer. Amplified 440–532 DNA fragments were digested with MboI restriction endonuclease and separated by electrophoresis in 15% or 10% polyacrylamide gels (30×40 cm). The undigested 93-bp PCR product and the 61-bp MboI cleavage product were excised from the gel and their associated radioactivity was determined by liquid scintillation counting. The identity of the 93-bp PCR product was confirmed by digestion with HinfI, specific for 472-T, and with PvuII, which cuts poliovirus type 3 RNA at position 491 (data not shown).

Two DNA fragments were synthesized for the construction of a standard set. A 93-bp fragment containing 100% 472-T was prepared by reverse transcription and PCR using a vaccine-derived RNA template and a modified pS primer (pS/T) containing an additional T residue at the 3' end, corresponding to 472-T. A 93-bp fragment containing 100% 472-C was made using RNA from a 472-C containing DM Pg35aP-396 strain of poliovirus type 3 vaccine (a gift of Dr. P. D. Minor) and a modified pS primer (pS/C) containing an additional C residue at the 3' end, corresponding to 472-C. These standard PCR amplified fragments containing 100% 472-T and 100% 472-C were mixed in different proportions and used as templates in PCR reactions. The amount of 472-C measured for every lot of vaccine was corrected using the calibration line obtained in the same experiment using the above described standard mixtures. In tests with some of the older vaccine preparations we observed a high background due to "smearing" of radioactive material which made the determination of 472-C abundance unreproducible. The reason for this smearing is unknown. The data with such samples were not included in the analysis.

Analysis of 2034-T to 2034-C mutants.

A DNA fragment corresponding to the genome region 1970–2070 of poliovirus type 3 genome was amplified using [$^{32}$P]-labelled sense primer (SEQ. ID. NO:3) and antisense primer (SEQ. ID. NO:4). The vaccine specific 2034-T containing sequence was detected by digestion with MseI restriction enzyme, and wild type-specific 2034-C containing sequence was detected by digestion with SfaNI restriction enzyme.

Analysis of mutations at positions 445, 448, 449.

A 124-p.b. DNA fragment corresponding to the genome region 409–532 of poliovirus type 3 genome was amplified using [$^{32}$P]-labelled antisense primer (SEQ. ID. NO:5). The latter corresponds to positions 409–441 of the type 3 poliovirus genome except for changes of A to T at position 422 (to remove a MboII restriction site) and A to T at position 433 (to remove an AluI restriction site). 445-A to 445-C mutants were detected by digestion of the 124-bp PCR-amplified fragment with HinfI and HgaI restriction enzymes which recognize the vaccine and mutant-specific sequences, respectively. 448-C to 448-G mutants were detected by digestion with MnlI (or HinfI) and Bsp1286 (restriction enzymes, recognizing the vaccine and wild type-specific sequences, respectively. 449-C to 449-A mutants were detected by digestion of the 124-mer with MnlI and FokI restriction endonucleases, cutting the vaccine and mutant-specific sequences, respectively.

RESULTS

We have hypothesized that the failure of some batches of type 3 poliovirus vaccine in the standard monkey neurovirulence test (WHO Tech. Rep. Ser, 687:107–175 (1983)) may be due to the presence in the vaccine preparations of 472-C mutants, previously shown to produce increased lesion scores in this test (Evans et al, Nature, 314:548–550 (1985)). To measure the relative abundance of 472-C mutants in mixed populations of the virus, we have developed an assay illustrated in FIG. 1. This assay is based on reverse transcription of viral RNA, followed by PCR amplification of a cDNA segment that includes position 472 and subsequent detection of sequences with the 472-T to 472-C substitution by digestion with a restriction enzyme. Since this substitution does not alter any known restrictions sites in the cDNA, we have mutated the sequence of the PCR product by using an imperfectly matched primer for second-strand cDNA synthesis and PCR. This modification leads to the appearance of a MboI restriction site that is characteristic for 472-C. The proportion of 472-C revertants is estimate after MboI digestion of single-end labeled PCR products by determining the proportion of radioactivity associated with MboI-digested fragments after separation in a polyacrylamide gel. The tested samples are analyzed in parallel with a series of standard cDNA mixtures, containing known proportions of 472-C (FIG. 2). Less than 0.2% of 472-C could be detected in these mixtures. The proportion of 472-C in the original cDNA template could be readily measured by this assay using a calibration curve (FIG. 3).

More than 40 lots of type 3 poliovirus vaccine produced from six different seed virus preparations were tested by the above assay. Almost all the batches contained measurable levels of 472-C mutants, indicating that such mutants were indeed present in the vaccine preparations. There was, however, a major difference in the frequency of 472-C mutants between the vaccines that passed versus those that failed in the required lesions score of standard monkey neurovirulence test. Six vaccine lots that failed this test had 472-C contents above 1.17%, whereas all the batches that passed the test contained less than 0.79% 472-C revertants (Table 1).

TABLE 1

Percent of 472-C in vaccines made from different seed viruses by different manufacturers. SO-I through SO-III are vaccines that were prepared from Sabin Original seed virus, RSO-I and RSO-II vaccines were prepared from RNA-plaque purified seed.

| Group | Number of vaccines in the group | Mean % C | Range |
| --- | --- | --- | --- |
| Failed monkey test | | | |
| SO-I | 2 | 1.39 ± 0.36 | 1.37 ± 0.19–1.40 ± 0.46 |
| SO-II | 3 | 1.98 ± 0.39 | 1.83 ± 0.40–2.21 ± 0.44 |
| SO-III | 1 | 1.17 ± 0.21 | |
| Total | 6 | 1.67 ± 0.52 | 1.17 ± 0.21–2.21 ± 0.44 |
| Passed monkey test | | | |
| SO-I | 9 | 0.58 ± 0.15 | 0.39 ± 0.09–0.79 ± 0.05 |
| SO-II | 1 | 0.28 ± 0.19 | |
| RSO-I | 14 | 0.12 ± 0.09 | 0–0.30 ± 0.03 |
| RSO-II | 10 | 0.32 ± 0.15 | 0.17 ± 0.07–0.49 ± 0.17 |
| Total | 34 | 0.29 ± 0.23 | 0–0.79 ± 0.05 |

Among the vaccines that passed the monkey tests, those that were prepared from Sabin Original (SO) seed virus stock (World Health Organization Requirements for poliomyelitis vaccine (oral). WHO Tech. Rep. Ser., 687:107–175 (1983)), were consistently higher in their 472-C content (Table 1) compared to vaccines prepared from an RNA-plaque purified (RSO) seed virus stock. WHO Tech. Rep. Ser., 687:107–175 (1983)). There were also differences in frequency of 472-C mutants among acceptable vaccines manufactured from different batches of the same seed virus (Table 1).

Figure 1:
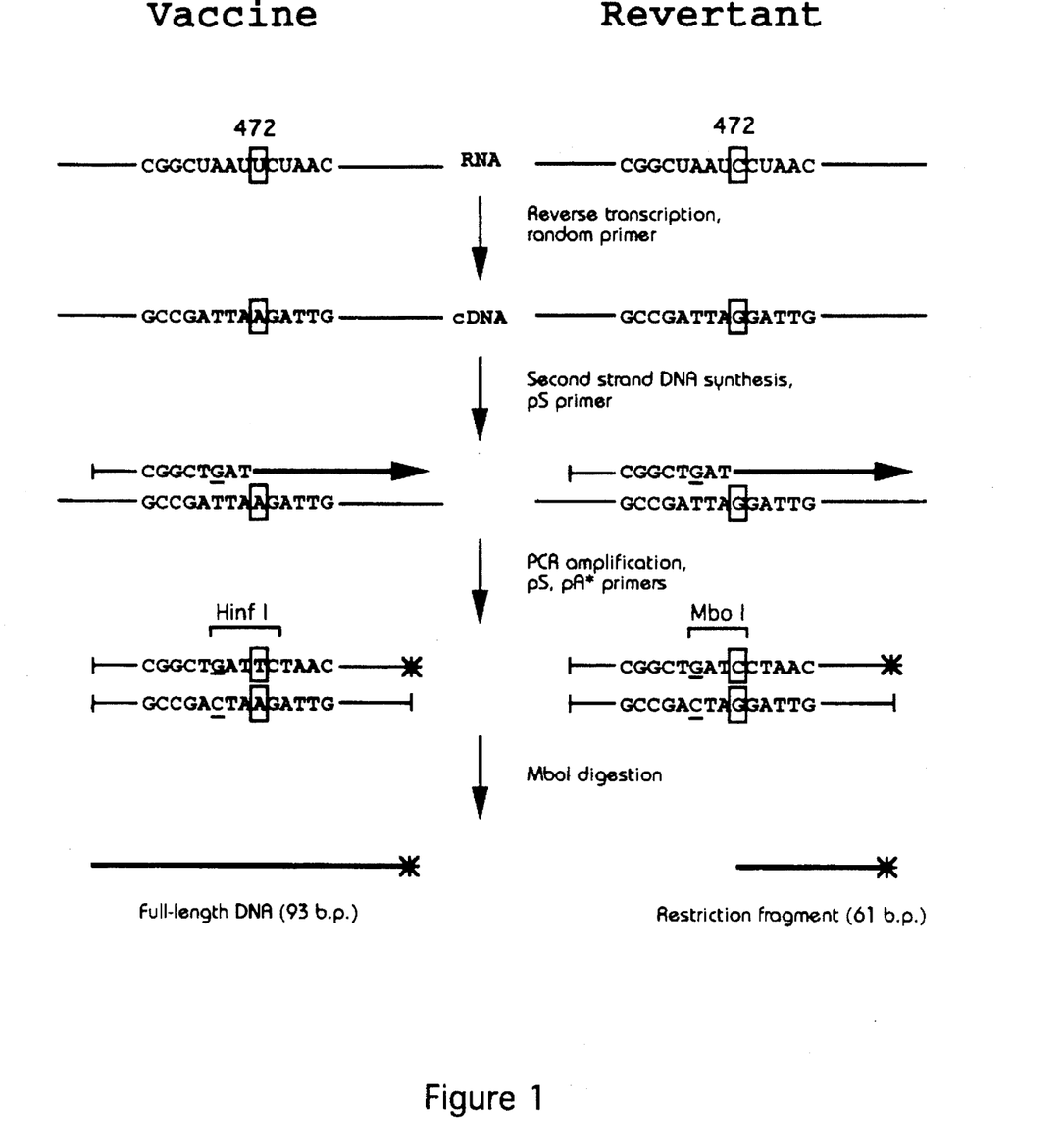
FIG. 1 is a scheme for detection of 472-U to 472-C mutation in polio vaccine type 3 RNA. The nucleotide at position 472 is boxed, and residue altered by use of mismatched primer is underlined. Asterisk indicates the primer and DNA fragments which are $^{32}$P-labeled at the 5' end.
Figure 2:
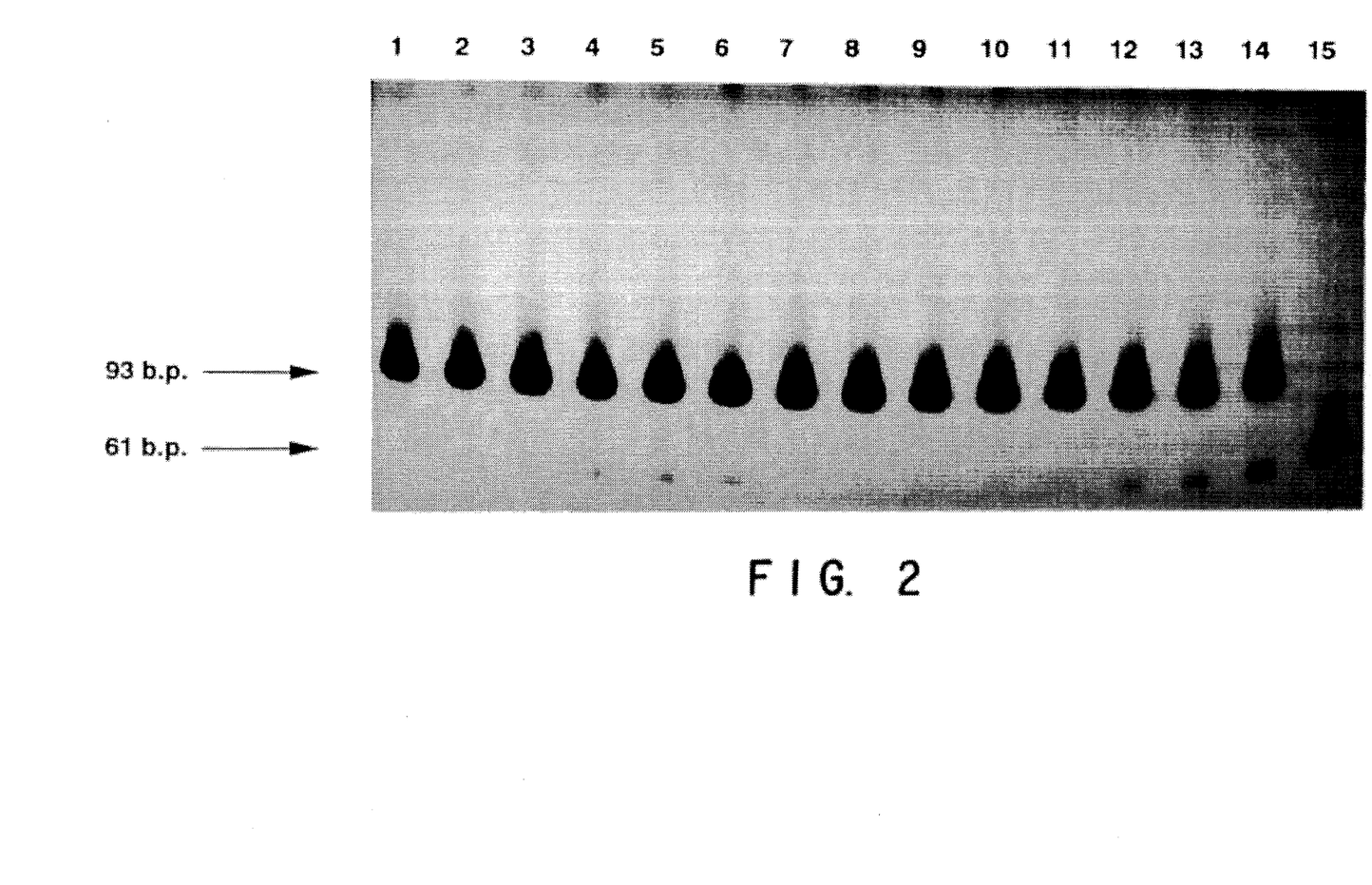
Figure 3:
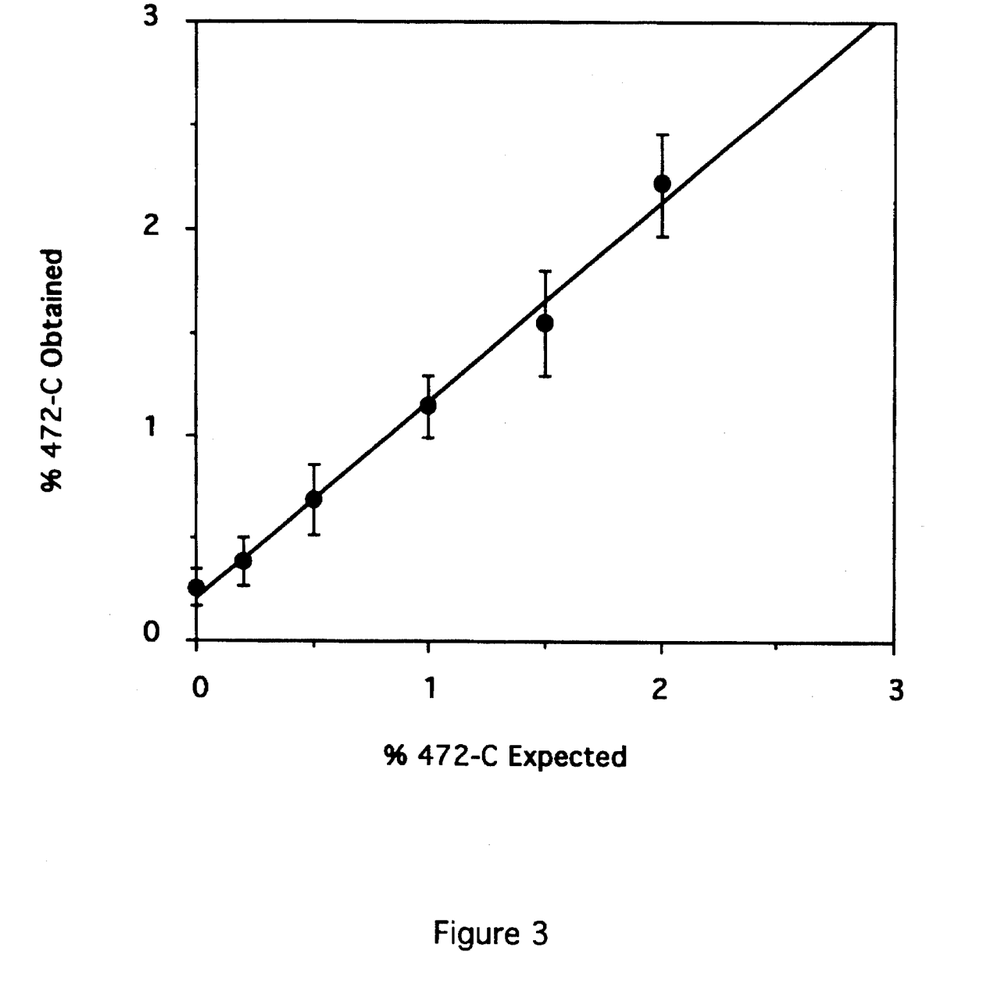
FIG. 3 is a calibration curve for quantitation of the proportion of 472-C revertants. The points correspond to the above described standard cDNA mixtures. Mean values and standard deviations from 15 experiments are presented.
Figure 4:
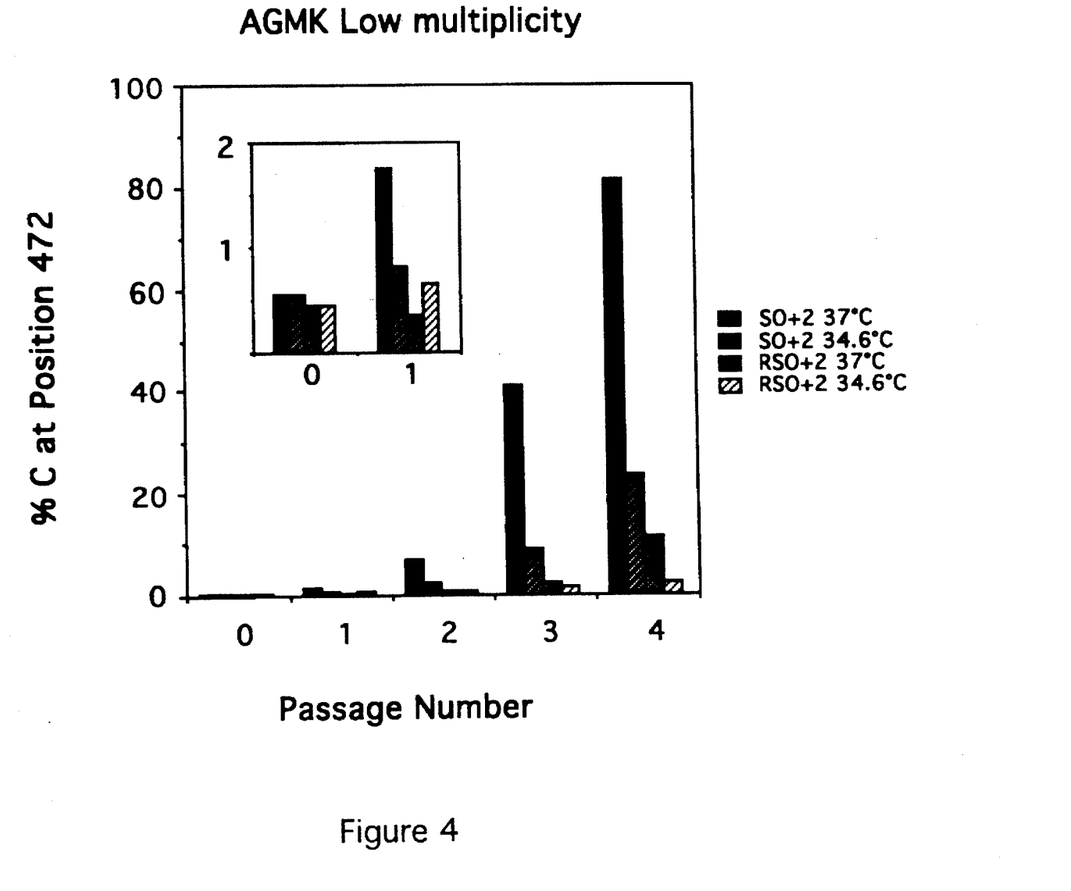
FIG. 4 is a bar graph which illustrates accumulation of 472-C in the course of passaging of two polio vaccine type 3 strains in AGMK cells. Bars represent the proportion of 472-C in the population of SO-derived and RSO-derived batches of vaccine during serial passages in AGMK cells either at 34.6° C. or at 37° C. Cells were infected at a low multiplicity (≈10.1 i.u./cell).
Figure 5:
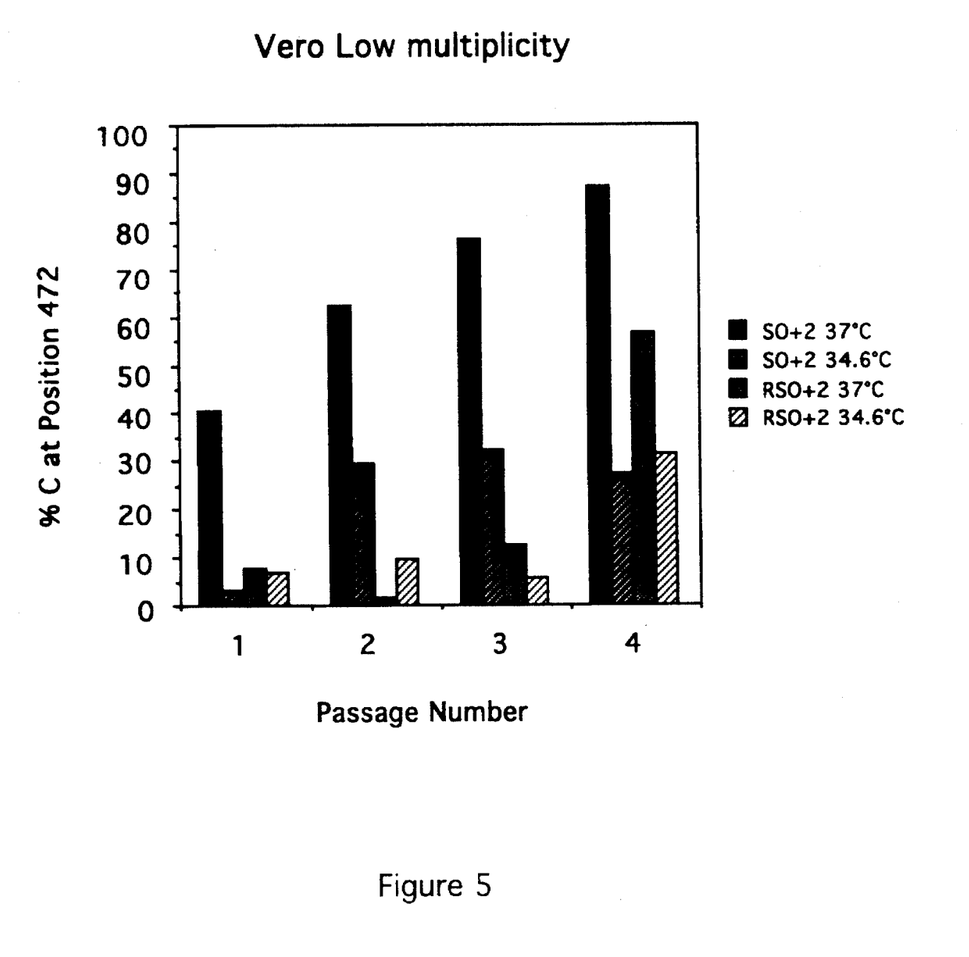
FIG. 5 is a bar graph which illustrates accumulation of 472-C in the course of passaging of two polio vaccine type 3 strains in Vero cells. Bars represent the proportion of 472-C in the population of SO-derived and RSO-derived batches of vaccine during serial passages in Vero cells either at 34.6° C. or at 37° C. Cells were infected at a low multiplicity (≈0.1 i.u./cell).

To identify the factors that may influence the frequency of 472-C mutants in vaccine preparations, we have asked if the proportion of these mutants is altered during serial passages of the vaccine virus in African green monkey kidney (AGMK) cells used for manufacturing the vaccine and whether the conditions of growth and the initial source of the virus affect this frequency. We have analyzed two vaccine preparations, one derived from SO and the other from RSO stock, after serial passage at 34.6° C. or 37° C. FIG. 4 demonstrates that at both temperatures 472-C mutants steadily accumulate in the course of passaging. This accumulation is much more rapid at 37° C. than at 34.6° C. and is more rapid for SO-derived virus than for RSO-derived virus. The rate of mutant accumulation was also influenced by the type of cells used for propagating the virus (WI-38 human diploid fibroblasts and Vero African green monkey kidney continuous cell line were used in these experiments) and by the multiplicity of infection during passages. FIG. 5 shows the accumulation of 472-C mutants in the course of passaging of type 3 poliovirus vaccine in Vero cells. The rate of mutants accumulation in these cells is much higher than in AGMK cells. These results indicate that selection for 472-C mutants occurs in the cells used for vaccine manufacturing and suggest that both the conditions for propagation of the virus, cell substrate used and the starting virus stock can determine the proportion of 472-C mutants in vaccine preparations.

The observed correlation between the results of the standard monkey neurovirulence test and the proportion of 472-C mutants confirms the significance of this position as an important marker of the original type 3 attenuated poliovirus strain.

Figure 6:
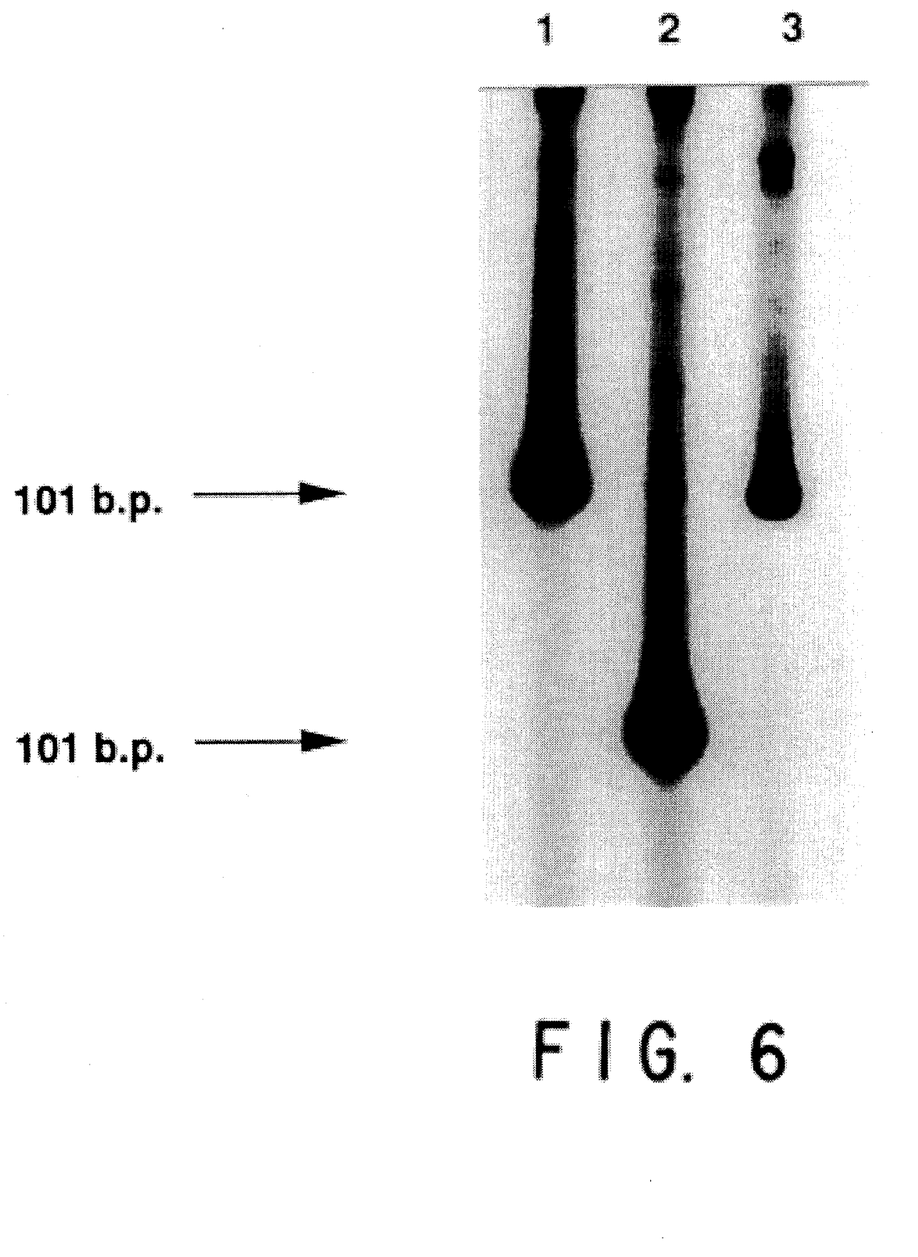
FIG. 6 is an autoradiogram of a polyacrylamide gel used in gel electrophoresis of PCR-amplified DNA fragment corresponding to positions 1970–2070 of type 3 OPV genome (WHO-III reference strain, corresponding to the second passage of the Sabin Original Leon $12a_1b$ strain in AGMK cells) digested with restriction enzymes that recognize 2034-T (MseI, lane 2) or 2034-C (SfaNI, lane 3). Lane 1 shows the uncut fragment.

We were interested to determine whether mutations in other regions of the viral genome can also contribute to an increased lesion score in the standard monkey test for acceptability of commercially produced lots of vaccine. In addition to 472, another position, 2034, has been suggested to play a functional role in the attenuation of poliovirus type 3 (Westrop et al, J. Virol., 63:1338–1344 (1989)). To test for reversion to the wild-type sequence at this position, we have amplified a DNA fragment spanning the region 1970–2070 of the virus genome and digested it with MseI restriction enzyme which is expected to cut the 2034-T-containing vaccine sequence and with SfaNI which should cut the 2034-C containing wild type sequence (FIG. 6). We were unable to find any detectable amount of 2034-C either in lots of type 3 OPV that failed or passed the monkey test, or in the vaccine virus that was passaged in cell culture under the conditions that favored the selection of 472-C revertants.

Weeks-Levy et al. (Weeks-Levy et al, Vaccines, 88:223–227 (1988)) reported that using direct sequencing they were able to detect mutations at positions 445, 448 and 449 in several type 3 poliovirus vaccine lots that failed the monkey test. To test for the presence of such mutations, we have amplified the DNA fragment corresponding to the region 409–532 of the virus genome and digested it with restriction enzymes that should discriminate between the vaccine and the mutated sequences (see Materials and Methods). We have found no mutations at any of these positions in 18 tested individual lots of vaccine which included those that failed and those that passed the standard monkey test (data not shown). In addition we have found that the sequence of the tested region is not (SEQ. ID NO. 6) (nucleotides 439 to 449) as given in (Weeks-Levy et al, Vaccines, 88:223–227 (1988)) but (SEQ. ID NO. 7) (nucleotides 439 to 448) (data not shown), which is in accord with the previously published data (Stanway et al, Nucleic Acids Res., 11:5629–5643 (1983) and Toyoda et al, J. Mol. Biol., 174:561–585 (1984)).

DISCUSSION

Neurovirulence of poliovirus has been shown to cover an extensive quantitative spectrum when tested by different routes (intrathalamic, intraspinal, oral, parenteral) in monkeys and chimpanzees (Sabin, Ann. N.Y. Acad. Sci., 61:924–938 (1955); Sabin, Brit. Med. J., 1:663–680 (1959); Sabin, PASB Sc. Pub., 44:14–33 (1959) and Sabin, J. Infect.

Dis., 151:420–436 (1985)). The standard monkey intraspinal neurovirulence test (World Health Organization Requirements for poliomyelitis vaccine (oral), WHO Tech. Rep. Ser., 687:107–175 (1983)) is based not on production of paralysis after the injection of different amounts of tissue culture virus directly into the anterior horns, but on the number of lesions (without paralysis) that are produced, i.e. the lesion score. This stringent test is purposefully designed to measure the least possible variation from the seed virus used to produce the vaccine lots for general use. Quantitative changes along the neurovirulence spectrum and changes of other properties have been demonstrated in the earliest work with the attenuated poliovirus used for vaccine production (Sabin, Ann. N.Y. Acad. Sci., 61:924–938 (1955); Sabin, Brit. Med. J., 1:663–680 (1959); Sabin, PASB Sc. Pub., 44:14–33 (1959) and Sabin, J. Infect. Dis., 151:420–436 (1985)), and recently some molecular changes have also been reported (Evans et al, Nature, 314:548–550 (1985) and Weeks-Levy et al, Vaccines, 88:223–227 (1988)).

The standard monkey test for acceptability of vaccine lots has been satisfactory used for almost 30 years. However, the test requires many monkeys, is expensive and shows the wide range of individual monkey's reactions. Accordingly, the demonstration in the present communication of a remarkable difference in the abundance of 472-C sequences between lots of type 3 OPV that pass the stringent monkey test and those that do not, provides an alternative molecular procedure for assessment of acceptability of vaccine lots.

We have shown that cultivation of the virus in vitro results in a rapid accumulation of 472-C, and the conditions of virus growth greatly influence the rate of mutant selection. It is noteworthy that two variants of type 3 OPV strain, on derived directly from the original stock of the seed virus and the other obtained by its RNA-plaque purification, differ in their rates of selection of 472-C despite the approximately equal proportion of mutants in the initial preparations. The selection seems to be specific for position 474, since analysis of another position, 2034, that was implicated in the increased neurovirulence (Westrop et al, J. Virol., 63:1338–1344 (1989)), or of positions 445, 448 and 449, reported to be altered in some vaccine lots (Weeks-Levy et al, Vaccines, 88:223–227 (1988)), showed no changes either in acceptable or unacceptable vaccine lots or after four experimental passages in AGMK cells in vitro.

The presence of C at position 472 apparently increases the translation efficiency of viral RNA (Svitkin et al, Virology, 175:103–109 (1990)); this increased efficiency is likely to provide the basis for the selective advantage of 472-C mutants during growth in AGMK cells, as well as in human gut (Evans et al, Nature, 314:548–550 (1985)) and in a neuroblastoma cell line (LaMonica et al, J. Virol., 63:2357–2360 (1989)).

Several specific mutations have also been implicated as the determinants of attenuation in type 1 and type 2 polioviruses (Moss et al, J. Virol., 63:1884–1890 (1989); Pollard et al, J. Virol., 63:4949–4951 (1989); Kawamura et al, J. Virol., 63:1302–1309 (1989) and Christodoulou et al. J. Virology, 64: 4922–4929 (1990)). The approach used in the present study can be applied to determine which mutations may be predictive for increased neurovirulence in vaccines of these two types. Our results suggest that molecular assay of the OPV may provide a supplement or an alternative to the current monkey test of the final product and may also be used for the in-process monitoring of poliovirus vaccine production. Furthermore, analysis of the mutant frequency at key positions associated with attenuation may also serve as a general principle for molecular evaluation of other attenuated viral or bacterial vaccines.

All publications including literature references cited are herein incorporated by reference.

We claim:

1. A method for classifying an unclassified live poliovirus type 3 vaccine, which is attenuated by a C to U substitution at nucleotide position 472, as having an acceptable or unacceptable level of neurovirulence in comprising the steps of:

quantifying revertant viruses contained in the vaccine prior to administration by testing for the presence of a U to C substitution at position 472 of the poliovirus type 3 genome; and comparing the percentage of revertant viruses in the unclassified vaccine to the percentage of revertant viruses in an accepted reference vaccine, which is attenuated by a C to U substitution at nucleotide position 472, a vaccine having a higher percentage of U to C substitution than in the reference vaccine being classified as unacceptable and a vaccine with an equal or lower percentage of U to C substitution than in the reference vaccine being classified as acceptable.

2. The method of claim 1, wherein the accepted reference vaccine is a vaccine that has passed the monkey neurovirulence test.

3. A method of classifying an unclassified live poliovirus type 3 vaccine as having an acceptable or unacceptable level of neurovirulence in comprising, prior to vaccine administration, the steps of:

a) selectively amplifying a region of a poliovirus type 3 vaccine genome containing nucleotide position 472 using selectively mismatched primers, whereby a restriction endonuclease site which includes nucleotide position 472 in the selectively amplified region is created by introducing a site-specific mutation into the amplified region;

b) digesting an amount of the amplified region of a) with a restriction endonuclease that specifically cleaves the amplified sequences in revertant viruses which contain a U to C substitution at nucleotide position 472;

c) digesting an amount of the amplified region of a) with a restriction endonuclease that specifically cleaves the amplified sequences in nonrevertant viruses which contain a U at nucleotide position 472;

d) quantifying the percentage of U to C revertant viruses in the unclassified vaccine; and e) comparing the percentage of revertant viruses in the unclassified vaccine to the percentage of revertant viruses in an accepted reference vaccine, which can pass the monkey neurovirulence test a vaccine with a higher percentage of U to C revertant viruses than in the reference vaccine being classified as unacceptable and a vaccine with an equal or lower percentage of U to C revertant viruses than in the reference vaccine being classified as acceptable.

4. The method of claim 3, wherein the amplification is by the polymerase chain reaction.

5. The method of claim 3, wherein the accepted reference vaccine is a vaccine that has passed the monkey neurovirulence test.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 32
        ( B ) TYPE: nucleic acid
        ( C ) STRANDEDNESS: single
        ( D ) TOPOLOGY: linear     ( i i ) MOLECULE TYPE:
        ( A ) DESCRIPTION: sense strand PCR primer     ( i v ) ANTI-SENSE: (N)

( x i ) SEQUENCE DESCRIPTION: SEQ ID NO: 1:

TGAGAGTCCT CCGGCCCTG AATGCGGCTG AT      3 2

( 2 ) INFORMATION FOR SEQ ID NO:2:

( i ) SEQUENCE CHARACTERISTICS:
        ( A ) LENGTH: 31
        ( B ) TYPE: nucleic acid
        ( C ) STRANDEDNESS: single
        ( D ) TOPOLOGY: linear     ( i i ) MOLECULE TYPE:

(A) DESCRIPTION: antisense strand PCR primer (iv) ANTI-SENSE: (Y)

(xi) SEQUENCE DESCRIPTION: SEQ ID NO: 2:

ACGGACTTGC GCGTTACGAC AGGCTGGCTG C    31

(2) INFORMATION FOR SEQ ID NO:3:

(i) SEQUENCE CHARACTERISTICS:
        (A) LENGTH: 35
        (B) TYPE: nucleic acid
        (C) STRANDEDNESS: single
        (D) TOPOLOGY: linear     (ii) MOLECULE TYPE:
        (A) DESCRIPTION: sense primer     (iv) ANTI-SENSE: (N)

(xi) SEQUENCE DESCRIPTION: SEQ ID NO: 3:

GTTACTCTGA GCGACAGTGC CGATCTATCG CAACC    35

(2) INFORMATION FOR SEQ ID NO:4:

(i) SEQUENCE CHARACTERISTICS:
        (A) LENGTH: 36
        (B) TYPE: nucleic acid
        (C) STRANDEDNESS: single
        (D) TOPOLOGY: linear     (ii) MOLECULE TYPE:
        (A) DESCRIPTION: antisense primer     (iv) ANTI-SENSE: (Y)

(xi) SEQUENCE DESCRIPTION: SEQ ID NO: 4:

ACTTCCCCAA GCATGGTGTG TGACAAGCGC GGATTA    36

(2) INFORMATION FOR SEQ ID NO:5:

(i) SEQUENCE CHARACTERISTICS:
        (A) LENGTH: 33
        (B) TYPE: nucleic acid
        (C) STRANDEDNESS: single
        (D) TOPOLOGY: linear     (ii) MOLECULE TYPE:
        (A) DESCRIPTION: sense primer     (iv) ANTI-SENSE: (N)

(xi) SEQUENCE DESCRIPTION: SEQ ID NO: 5:

GAACAGGGTG TGATGAGGCC TATTGTGCTA CTG    33

(2) INFORMATION FOR SEQ ID NO:6:

(i) SEQUENCE CHARACTERISTICS:
        (A) LENGTH: 11
        (B) TYPE: nucleic acid
        (C) STRANDEDNESS: single
        (D) TOPOLOGY: linear     (ii) MOLECULE TYPE:
        (A) DESCRIPTION: published sequence of nucleotides 439-446
            of poliovirus type 3 genome     (xi (2) INFORMATION FOR SEQ ID NO:7:

(i) SEQUENCE CHARACTERISTICS:
        (A) LENGTH: 10
        (B) TYPE: nucleic acid
        (C) STRANDEDNESS: single
        (D) TOPOLOGY: linear     (ii) MOLECULE TYPE:
        (A) DESCRIPTION: correct sequence of nucleotides 439-448 of poliovirus type 3 genome     (xi) SEQUENCE DESCRIPTION: SEQ ID NO: 7:

AUGAGAGUCC          10